United States Patent
Jung et al.

[11] Patent Number: 6,022,987
[45] Date of Patent: Feb. 8, 2000

[54] ARYL SUBSTITUTED ALKYLSILANES AND A PREPARATION METHOD THEREOF

[75] Inventors: Il Nam Jung, Seoul; Bok Ryul Yoo, Koyang; Joon Soo Han, Seoul; Yeon Seok Cho, Seoul, all of Rep. of Korea

[73] Assignee: Korea Institute of Science and Technology, Seoul, Rep. of Korea

[21] Appl. No.: 08/997,583

[22] Filed: Dec. 23, 1997

[30] Foreign Application Priority Data

Dec. 30, 1996 [KR] Rep. of Korea ............... 96-77559

[51] Int. Cl.$^7$ ............................................. C07F 7/08
[52] U.S. Cl. ................................... 556/489; 552/101
[58] Field of Search .................... 556/489; 552/101

[56] References Cited

U.S. PATENT DOCUMENTS

| | | | |
|---|---|---|---|
| 3,423,445 | 1/1969 | Holbrook et al. | 556/489 |
| 3,465,017 | 9/1969 | Coutant | 556/489 |
| 5,386,050 | 1/1995 | Jung et al. | 556/489 |
| 5,527,938 | 6/1996 | Jung et al. | 556/489 |
| 5,710,301 | 1/1998 | Fujiki | 556/430 |

OTHER PUBLICATIONS

Roberts et al., *Friedel–Crafts Alkylation Chemistry* (cover page), 1984.
Chernyshev et al., *Zhur. Obshchei Khim.* 25:2469–74 (1955), Chemical Abstract No. 50, 9313a.
Chernyshev et al., *Zhur Obshchei Khim.* 25:613–16 (1958), Chemical Abstract No. 52, 1715b.
Chernyshev et al., *Zhur. Obshchei Khim.* 28:2829–37 (1958), Chemical Abstract No. 53, 9110c.
Krieble et al., *J. Ame. Chem.* Soc. 67:1810–1812, 1945.

*Primary Examiner*—Paul F. Shaver
*Attorney, Agent, or Firm*—Darby & Darby

[57] ABSTRACT

Aryl substituted alkylsilanes represented by the formula I and a preparation method thereof by reacting substituted benzenes represented by the formula II with aryl substituted alkylsilanes represented by the formula III in the presence of Lewis acid catalysts such as aluminum chloride:

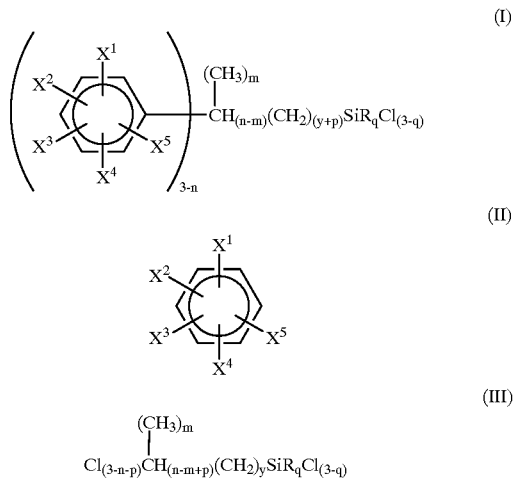

wherein m, p, and q are 0 or 1, respectively; n and y are 0, 1, or 2, respectively; $X^1$, $X^2$, $X^3$, $X^4$, and $X^5$ which are same or different represent hydrogen, fluoro, chloro; R represents $C_1$–$C_{12}$ alkyl group; provided that if n is 0, m is 0 and if n is 1 or 2, at least two of $X^1$, $X^2$, $X^3$, $X^4$, and $X^5$ represent chloro or fluoro group.

20 Claims, No Drawings

ARYL SUBSTITUTED ALKYLSILANES AND A PREPARATION METHOD THEREOF

BACKGROUND OF THE INVENTION

The present invention relates to aryl substituted alkylsilanes and a preparation method thereof. More particularly, the present invention relates to aryl substituted alkylsilanes and a preparation method thereof by reacting substituted benzenes with aryl substituted alkylsilanes in the presence of Lewis acid catalysts.

Since Friedel and Crafts first reported the alkylation reaction of benzene with alkyl halide in the presence of aluminum chloride catalyst in 1877, the Friedel-Crafts type alkylation reaction has been widely used as a synthetic procedure in organic synthesis(R. M. Roberts and A. A. Khalaf, *Friedel-Crafts Alkylation Chemistry*, Marcel Dekker, Inc., NY, 1984).

Chernyshev and Dolgaya reported the Friedel-Crafts type alkylation of (chloroalkyl)trichlorosilanes to substituted benzenes to produce (trichlorosilyl)-alkylbenzenes [E. A. Chernyshev and M. E. Dolgaya, *Zhur. Obschchei Khim*, 25, 2469(1955)].

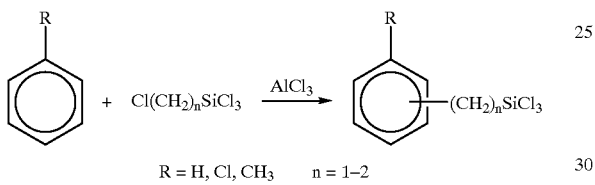

R = H, Cl, CH$_3$  n = 1–2

They reacted (dichloromethyl)silane or (dichloroethyl)silane with benzene, chlorobenzene, or toluene to produce two phenyl groups substituted alkylchlorosilanes [E. A. Chernyshev, M. E. Dolgaya, and A. D. Petrov, *Zhur. Obschchei Khim*, 28, 613 (1958)]. They also reacted (chloropropyl)silane with benzene, chlorobenzene, toluene, biphenyl, or biphenyl ether to produce phenyl groups substituted propylchlorosilanes [E. A. Chernyshev, M. E. Dolgaya, and Yu. P. Egorov, *Zhur. Obschchei Khim*, 28, 2829(1958)].

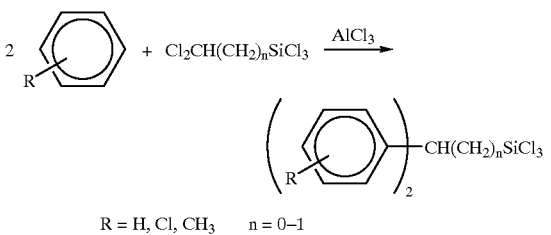

R = H, Cl, CH$_3$  n = 0–1

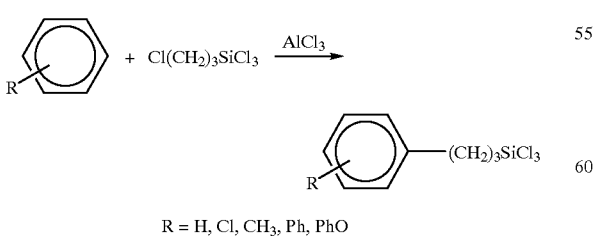

R = H, Cl, CH$_3$, Ph, PhO

Recently, we reported the Friedel-Crafts type alkylation of substituted benzenes with allyldichlorosilanes (Jung, I. N.; Yoo, B. R.; Lee, B. W.; Yeon, S. H., U.S. Pat. No. 5,527,938) and vinylchlorosilanes (Korea Patent Application No. 95-48114).

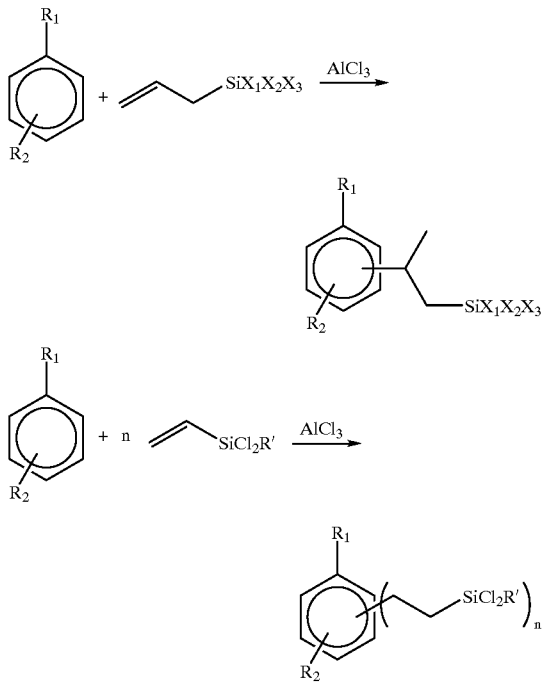

(Chloroalkyl)silanes can be easily prepared by the photochlorination of alkylsilanes on a large scale. In this process, polychlorinated alkylsilanes are inevitably produced as byproducts, because the chlorinated organic moieties are more susceptible toward the chlorination [R. H. Krieble and J. R. Elliott, *J. Am. Chem. Soc.*, 67, 1810 (1945)]. However, polychlorinated alkylsilanes do not find any applications in industry and are disposed. Thus, it is very important to develop a method to convert the polychlorinated byproducts from chlorination reactions of alkylchlorosilanes to useful organosilane compounds. We found that the chloro groups of polychlorinated alkylsilanes can be converted to the corresponding polyaryl substituted alkylsilanes by the Friedel-Crafts type alkylation with particularly more than two halogen atoms substituted benzenes in the presence of Lewis acid catalysts. This method can be applied to the alkylsilane compounds having not only one or two chlorine atoms but also three chlorines.

SUMMARY OF THE INVENTION

It is an object of the present invention to provide aryl substituted alkylsilanes represented by the formula (I).

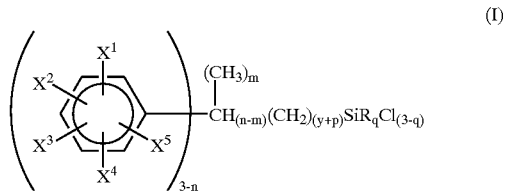

(I)

(wherein m, p, and q are 0 or 1, respectively; n and y are 0, 1, or 2, respectively; $X^1$, $X^2$, $X^3$, $X^4$, and $X^5$ which are same or different represent hydrogen, fluoro, chloro; R represents C$_1$–C$_{12}$ alkyl group; provided that if n is 0, m is 0 and if n is 1 or 2, at least two of $X^1$, $X^2$, $X^3$, $X^4$, and $X^5$ represent chloro or fluoro group).

Another object of the present invention is to provide a method for preparing aryl substituted alkylsilanes which comprises reacting substituted benzenes of the formula (II) with (polychloroalkyl)silane of the formula (III) in the presence of Lewis acid catalysts such as aluminum chloride:

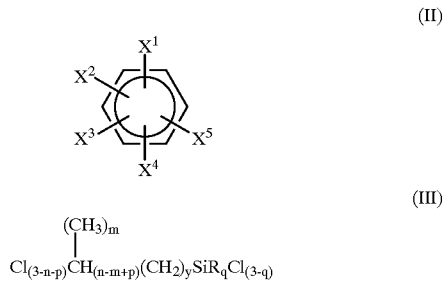

(II)

$$Cl_{(3-n-p)}CH_{(n-m+p)}(CH_2)_y SiR_q Cl_{(3-q)}$$

(III)

(wherein, m, p, q, n, y, $X^1$, $X^2$, $X^3$, $X^4$, and $X^5$ have the same definition as in the formula (I))

The manner in which the foregoing and other objects of this invention are accomplished will be apparent from the accompanying specification and claims considered together with the working examples.

DETAILED DESCRIPTION OF THE INVENTION

The preparation of aryl substituted alkylsilanes containing more than two halogen groups on the aromatic ring according to the present invention can be run in standard laboratory glassware or commercial equipments, under inert atmosphere, with units for external heating and cooling, stirring, and for incremental addition of the start silanes. The reaction can be carried out in neat or in most of nonaromatic or nonprotic solvents such as hexane or dichloromethane. In a typical preparation, substituted benzenes and polychlorinated alkylsilane represented by the formula III are placed in the reactor under inert atmosphere. Substituted benzenes and (polychloroalkyl)silanes are used in the molar ratio of 1 to 20:1. Aluminum chloride or Aluminum is the best catalyst and can be used alone or in junction with other Lewis acid such as chlorides of zinc, boron, iron, tin, titanium and antimony. The (polychloroalkyl)silane is then slowly added to the reactants in the reactor with stirring at the reaction temperatures between 0° C. and 200° C. The amount of Lewis acid used is 1–100 mole %, preferably 5–50 mole % of polychlorinated alkylsilanes. After completion of addition, the solution may be kept stirring for a certain period of time to complete the alkylation and then the products may be fractionally distilled at atmosphere or under vacuum.

The invention will be further illustrated by the following examples, but not limited to the examples given.

EXAMPLE 1

Alkylation of 1,4-dichlorobenzene with (Dichloromethyl)Methyldichlorosilane

To a 250 ml, three-necked, frame dried, round bottom flask equipped with a magnetic stirrer, a reflux condenser, and a dropping funnel, aluminum chloride 1.28 g (9.60 mmol) and 1,4-dichlorobenzene 62.89 g (428 mmol) were placed under dry nitrogen atmospheric pressure. After (dichloromethyl) methyldichlorosilane 14.12 g (72.31 mmol) was added to the solution, the reaction mixture was heated for 7 hours at 150° C. The aluminum chloride catalyst was quenched with $POCl_3$ 1.47 g (9.59 mmol) and then stirred for another 1 hour to complete the deactivation. Freshly distilled hexane (100 ml) was added to the reaction mixture and insoluble solids in hexane were filtered from the organic soultion. After hexane was distilled, the reaction products were vacuum distilled at 0.2 torr to give 14.14 g of [bis(2,5-dichlorophenyl)methyl] methyldichlorosilane (bp; 154° C./0.2 torr, yield; 47%).

$^1$H-NMR($CDCl_3$, ppm) 0.86 (s, 3H, SiC$\underline{H}_3$), 5.05 (s, 1H, C$\underline{H}$), 7.20–7.58 (m, 6H, Ar$\underline{H}$)

$^{13}$C-NMR($CDCl_3$, ppm) 5.3 ($\underline{C}H_3$), 39.5 ($\underline{C}H$), 128.6, 130.8, 131.2, 132.9, 133.4, 136.7 (Ar$\underline{C}$)

EXAMPLE 2

Alkylation of Fluorobenzene with (Dichloromethyl) Methyldichlorosilane

In a 100 ml, three-necked, frame dried, round bottom flask, aluminum chloride 1.679 (12.5 mmol), fluorobenzene 37.93 ml (404 mmol), and (dichloromethyl) methyldichlorosilane 7.08 ml (50.5 mmol) were reacted for 2 hours as in EXAMPLE 1. The aluminum chloride catalyst was quenched with $POCl_3$ 1.15 ml (12.5 mmol) and then stirred for another 1 hour to complete the deactivation. Freshly distilled hexane (50 ml) was added to the reaction mixture and insoluble solids in hexane were filtered from the organic solution. After hexane and fluorobenzene were distilled, the reaction products were vacuum distilled to give 10.49 g of [bis(fluorophenyl)methyl]methyldichlorosilane as a mixture of isomers (bp; 103° C./0.2 torr, yield; 65%).

$^1$H-NMR($CDCl_3$, ppm) 0.79–0.89 (3H, SiCH$_3$), 4.01–4.78 (1H, CH), 6.97–7.58 (8H, ArH)

EXAMPLE 3

Alkylation of Benzene with (Trichloromethyl) Methyldichlorosilane

In the same apparatus and procedures as EXAMPLE 1 above, 50.4 ml (564 mmol) of benzene and 2.92 g (21.9 mmol) of aluminum chloride were alkylated with 10.0 g (43.0 mmol) of (trichloromethyl)methyldichlorosilane under dry nitrogen atmospheric pressure for 5 hours at room temperature. The aluminum chloride catalyst was quenched with $POCl_3$ and then stirred for another 1 hour to complete the deactivation. Freshly distilled hexane (100 ml) was added to the reaction mixture and insoluble solids in hexane were filtered from the organic soultion. After hexane and benzene were distilled, recrystallization from chloroform yielded 3.58 g of (triphenylmethyl)methyldichlorosilane (mp: 170–172° C., yield; 23%).

$^1$H-NMR($CDCl_3$, ppm) 0.88 (s, 3H, SiC$\underline{H}_3$), 7.19–7.33 (m, 15H, Ar$\underline{H}$)

13C-NMR($CDCl_3$, ppm) 7.9 ($\underline{C}H_3$), 57.5 ($\underline{C}$—Si), 126.8, 128.3, 130.4, 142.9(Ar$\underline{C}$)

EXAMPLE 4

Alkylation of Benzene with (Trichloromethyl) Trichlorosilane

In the same apparatus and procedures as EXAMPLE 2 above, 22.88 ml (256 mmol) of benzene and 0.80 g (6.0 mmol) of aluminum chloride were alkylated with 9.04 g (17.2 mmol) of (trichloromethyl)trichlorosilane under dry nitrogen atmospheric pressure for 1 hr at 50° C. The aluminum chloride catalyst was quenched with POCl$_3$ and then stirred for another 1 hour to complete the deactivation. Freshly distilled hexane(50 ml) was added to the reaction mixture and insoluble solids in hexane were filtered from the organic soultion. After hexane and benzene were distilled, recrystallization from chloroform yielded 1.23 g of (triphenylmethyl)trichlorosilane (mp; 195–7: É, yield; 19%).

$^1$H-NMR(CDCl$_3$, ppm) 7.17–7.32 (m, 15H, ArH)

EXAMPLE 5

Alkylation of 1,4-dichlorobenzene with (2,2-dichloroethyl)Trichlorosilane

In the same apparatus and procedures as EXAMPLE 2 above, 14.70 g (100 mmol) of 1,4-dichlorobenzene and 0.027 g (1.0 mmol) of aluminum foil were alkylated with 4.98 g (21.4 mmol) of (2,2-dichloroethyl)trichlorosilane for 1 hour at 80° C. Freshly distilled hexane (50 ml) was added to the reaction mixture and insoluble solids in hexane were filtered from the organic soultion. After hexane and benzene were distilled, the reaction products were vacuum distilled to give 3.33 g of [2,2-bis(2,5-dichlorophenyl)ethyl] trichlorosilane (bp; 161–163° C./1 torr, yield; 59%).

$^1$H-NMR(CDCl$_3$, ppm) 2.17 (d, J=7.8 Hz, 2H, CH$_2$), 5.26 (t, J=7.8 Hz, 1H, CH), 7.19–7.36 (m, 6H, ArH)

EXAMPLE 6

Alkylation of Benzene with (3,3-dichloropropyl) Trichlorosilane

In the same apparatus and procedures as EXAMPLE 2 above, 36.0 ml (405 mmol) of benzene and 0.53 g (4.0 mmol) of aluminum chloride were alkylated with 10.08 g (41.0 mmol) of (3,3-dichloropropyl)trichlorosilane. The aluminum chloride catalyst was quenched with POCl$_3$ and then stirred for another 1 hour to complete the deactivation. Freshly distilled hexane (50 ml) was added to the reaction mixture and insoluble solids in hexane were filtered from the organic soultion. After hexane and benzene were distilled, the reaction products were vacuum distilled to give 6.76 g of (3,3-diphenylpropyl)trichlorosilane (bp; 124–125° C./0.5 torr, yield; 50%).

$^1$H-NMR(CDCl$_3$, ppm) 1.4 (t, J=8.0, 2H, CH$_2$Si), 2.36 (q, J=8.0 Hz, 2H, CH$_2$), 3.97 (t, J=8.0 Hz, 1H, CH), 7.05–7.38 (m, 10H, ArH).

EXAMPLE 7

Alkylation of Fluorobenzene with (3,3-dichloropropyl)Trichlorosilane

In the same apparatus and procedures as EXAMPLE 2 above, 18.8 ml (200 mmol) of fluorobenzene and 0.035 g (1.3 mmol) of aluminum foil were alkylated with 6.42 g (26.1 mmol) of (3,3-dichloropropyl)trichlorosilane for 2 hours at 70° C. Freshly distilled hexane(50 ml) was added to the reaction mixture and insoluble solids in hexane were filtered from the organic soultion. After hexane and fluorobenzene were distilled, the reaction products were vacuum distilled to give 4.50 g of [3,3-bis(fluorophenyl)propyl] trichlorosilanes as a mixture of isomers (bp; 121–122° C./0.5 torr, yield; 47%).

$^1$H-NMR(CDCl$_3$, ppm) 1.32–1.45 (2H, CH$_2$Si), 2.22–2.34 (2H, CH$_2$CH$_2$Si), 3.89–3.95, 4.25–4.32, 4.57–4.63 (1H, CH), 6.90–7.31 (8H, ArH)

EXAMPLE 8

Alkylation of Benzene with (1,2-dichloroethyl) Trichlorosilane

In the same apparatus and procedures as EXAMPLE 2 above, 25.2 ml (282 mmol) of benzene and 0.80 g (6.0 m) of aluminum chloride were alkylated with 6.60 g (28.2 mmol) of (1,2-dichloroethyl)trichlorosilane for 20 min at 70° C. The aluminum chloride catalyst was quenched with POCl$_3$ and then stirred for another 1 hour to complete the deactivation. Freshly distilled hexane(50 ml) was added to the reaction mixture and insoluble solids in hexane were filtered from the organic soultion. After hexane and benzene were distilled, the reaction products were vacuum distilled to give 4.82 g of (2,2-diphenylethyl)trichlorosilane (bp; 117° C./0.5 torr, yield; 54%).

$^1$H-NMR(CDCl$_3$, ppm) 2.33 (d, J=7.7 Hz, 2H, CH$_2$), 4.44 (t, J=7.7 Hz, 1H, CH), 7.22–7.34 (m, 10H, ArH)

EXAMPLE 9

Alkylation of 1,4-dichlorobenzene with (1,2-dichloroethyl)Trichlorosilane

In the same apparatus and procedures as EXAMPLE 2 above, 17.35 g (118 mmol) of 1,4-dichlorobenzene and 0.47 g (3.5 mmol) of aluminum chloride were alkylated with 5.45 g (23.5 mmol) of (1,2-dichloroethyl)trichlorosilane for 20 min at 120° C. The aluminum chloride catalyst was quenched with POCl$_3$ and then stirred for another 1 hour to complete the deactivation. Freshly distilled hexane (50 ml) was added to the reaction mixture and insoluble solids in hexane were filtered from the organic soultion. After hexane was distilled, the reaction products were vacuum distilled to give 4.56 g of [2,2-bis(2,5-dichlorophenyl)ethyl] trichlorosilane (bp; 161–163° C./0.5 torr, yield; 43%).

$^1$H-NMR(CDCl$_3$, ppm) 2.17 (d, J=7.8 Hz, 2H, CH$_2$), 5.26 (t, J=7.8 Hz, 1H, CH), 7.19–7.36 (m, 6H, ArH)

EXAMPLE 10

Alkylation of 1,3-dichlorobenzene with (1,2-dichloroethyl)Trichlorosilane

In the same apparatus and procedures as EXAMPLE 1 above, 49.1 ml (430 mmol) of 1,3-dichlorobenzene and 2.30 g (17.2 mmol) of aluminum chloride were alkylated with 19.40 g (83.5 mmol) of (1,2-dichloroethyl)trichlorosilane for 30 min at 120° C. The aluminum chloride catalyst was quenched with POCl$_3$ and then stirred for another 1 hour to complete the deactivation. Freshly distilled hexane (100 ml) was added to the reaction mixture and insoluble solids in hexane were filtered from the organic soultion. After hexane was distilled, the reaction products were vacuum distilled to give 14.6 g of [2,2-bis(2,4-dichlorophenyl)ethyl] trichlorosilane (bp; 175–180° C./0.5 torr, yield; 39%).

$^1$H-NMR(CDCl$_3$, ppm) 2.17 (d, J=7.6 Hz, 2H, CH$_2$), 5.26 (t, J=7.6 Hz, 1H, CH), 7.13–7.42 (m, 6H, ArH)

EXAMPLE 11

Alkylation of 1,2,4-trichlorobenzene with (1,2-dichloroethyl)Trichlorosilane

In the same apparatus and procedures as EXAMPLE 2 above, 21.5 ml (172 mmol) of 1,2,4-trichlorobenzene and 0.92 g (6.9 mmol) of aluminum chloride were alkylated with 8.17 g (35.2 mmol) of (1,2-dichloroethyl)trichlorosilane for 10 min at at 120° C. The aluminum chloride catalyst was quenched with POCl₃ and then stirred for another 1 hour to complete the deactivation. Freshly distilled hexane (50 ml) was added to the reaction mixture and insoluble solids in hexane were filtered from the organic soultion. After hexane was distilled, the reaction products were vacuum distilled to give 10.70 g of [2,2-bis(trichlorophenyl)ethyl] trichlorosilane as a mixture of isomers (bp; 192–194° C./0.5 torr, yield; 58%).

$^1$H-NMR(CDCl₃, ppm) 2.14 (d, J=7.8 Hz, 2H, C$\underline{H}_2$), 5.16 (t, J=7.6 Hz, 1H, C$\underline{H}$), 7.27, 7.53 (S, 4H, Ar$\underline{H}$)

EXAMPLE 12

Alkylation of 1,2,3,4-tetrachlorobenzene with (1,2-dichloroethyl)Trichlorosilane In the same apparatus and procedures as EXAMPLE 1 above, 43.18 g (200 mmol) of 1,2,3,4-tetrachlorobenzene and 1.07 g (8.0 mmol) of aluminum chloride were alkylated with 9.30 g (40.0 mmol) of (1,2-dichloroethyl) trichlorosilane for 10 min at 130° C. The aluminum chloride catalyst was quenched with POCl₃ and then stirred for another 30 min to complete the deactivation. Freshly distilled hexane(100 ml) was added to the reaction mixture and insoluble solids in hexane were filtered from the organic soultion. After hexane was distilled, the reaction products were vacuum distilled to give 10.41 g of [2,2-bis(2,3,4,5-tetrachlorophenyl) ethyl]trichlorosilane (bp; 218–222° C./0.5 torr, yield; 44%).

$^1$H-NMR(CDCl₃, ppm) 2.11 (d, J=7.7 Hz, 2H, C$\underline{H}_2$), 5.12 (t, J=7.7 Hz, 1H, C$\underline{H}$), 7.28 (S, 2H, Ar$\underline{H}$)

EXAMPLE 13

Alkylation of Benzene with (2,3-dichloropropyl) Trichlorosilane

In the same apparatus and procedures as EXAMPLE 2 above, 17.8 ml (200 mmol) of benzene and 0.27 g (2.0 mmol) of aluminum chloride were alkylated with 4.51 g (18.3 mmol) of (2,3dichloropropyl)trichlorosilane for 10 min at 70° C. The aluminum chloride catalyst was quenched with POCl₃ and then stirred for another 30 min to complete the deactivation. Freshly distilled hexane (50 ml) was added to the reaction mixture and insoluble solids in hexane were filtered from the organic soultion. After hexane and benzene were distilled, the reaction products were vacuum distilled to give 2.91 g of (3,3-diphenylpropyl)trichlorosilane (bp; 124–125° C./0.5 torr, yield; 48%).

$^1$H-NMR(CDCl₃, ppm) 1.40 (t, J=8.0, 2H, C$\underline{H}_2$si), 2.36 (q, J=8.0 Hz, 2H, C$\underline{H}_2$), 3.97 (t, J=8.0 Hz, 1H, C$\underline{H}$), 7.05–7.38 (m, 10H, Ar$\underline{H}$)

EXAMPLE 14

Alkylation of Fluorobenzene with (2,3-dichloropropyl)Trichlorosilane

In the same apparatus and procedures as EXAMPLE 2 above, 18.8 ml (200 mmol) of fluorobenzene and 0.31 g (2.3 mmol) of aluminum chloride were alkylated with 5.61 g (22.8 mmol) of (2,3-dichloropropyl)trichlorosilane for 10 min at 70° C. The aluminum chloride catalyst was quenched with POCl₃ and then stirred for another 1 hour to complete the deactivation. Freshly distilled hexane (50 ml) was added to the reaction mixture and insoluble solids in hexane were filtered from the organic soultion. After hexane and fluorobenzene were distilled, the reaction products were vacuum distilled to give 3.39 g of [3,3-bis(fluorophenyl)propyl] trichlorosilane (bp; 121–122° C./0.5 torr, yield; 41%) as a mixutre of isomers.

$^1$H-NMR(CDCl$_{31}$ ppm) 1.32–1.45 (m, 2H, C$\underline{H}_2$Si), 2.22–2.34 (m, 2H, C$\underline{H}_2$CH₂Si), 3.89–3.95, 4.25–4.32, 4.57–4.63 (m, 1H, C$\underline{H}$), 6.90–7.31 (m, 8H, Ar$\underline{H}$)

EXAMPLE 15

Alkylation of Benzene with (2,3-dichlorobutyl) Trichlorosilane

In the same apparatus and procedures as EXAMPLE 2 above, benzene 24.1 ml (270 mmol) and 0.72 g (5.4 mmol) of aluminum chloride were alkylated with 7.17 g (27.5 mmol) of (2,3-dichlorobutyl)trichlorosilane for 10 min at 70° C. The aluminum chloride catalyst was quenched with POCl₃ and then stirred for another 1 hour to complete the deactivation. Freshly distilled hexane (50 ml) was added to the reaction mixture and insoluble solids in hexane were filtered from the organic soultion. After hexane and benzene were distilled, the reaction products were vacuum distilled to give 2.31 g of (3,3-diphenylbutyl)trichlorosilane (bp; 122–124° C./0.5 torr, yield; 24%).

$^1$H-NMR(CDCl₃, ppm) 1.20 (t, J=8.0 Hz, 2H, C$\underline{H}_2$Si), 1.70 (s, 3H, CH₃), 2.38 (t, J=8.0 Hz, 2H, C$\underline{H}_2$CH₂Si), 6.95–7.37 (m, 10H, Ar$\underline{H}$)

EXAMPLE 16

Alkylation of 1,3-dichlorobenzene with (2,3-dichlorobutyl)Trichlorosilane

In the same apparatus and procedures as EXAMPLE 2 above, 26.3 ml (230 mmol) of 2,3-dichlorobenzene and 1.23 g (9.2 mmol) of aluminum chloride were alkylated with 11.91 g (45.7 mmol) of (2,3-dichlorobutyl)trichlorosilane for 20 min at 90° C. The aluminum chloride catalyst was quenched with POCl₃ and then stirred for another 30 min to complete the deactivation. Freshly distilled hexane (50 ml) was added to the reaction mixture and insoluble solids in hexane were filtered from the organic soultion. After hexane and benzene were distilled, the reaction products were vacuum distilled to give 5.06 g of [3,3-bis(2,4-dichlorophenyl)butyl]trichlorosilane (bp; 186– 190° C./0.5 torr, yield; 23%).

$^1$H-NMR(CDCl₃, ppm) 1.12 (t, J=7.8 Hz, 2H, C$\underline{H}_2$Si), 1.50 (s, 3H, CH₃), 2.44 (t, J=7.8 Hz, 2H, C$\underline{H}_2$CH₂Si), 7.13–7.55 (m, 6H, Ar$\underline{H}$)

What is claimed is:

1. Aryl substituted alkylsilanes represented by formula I.

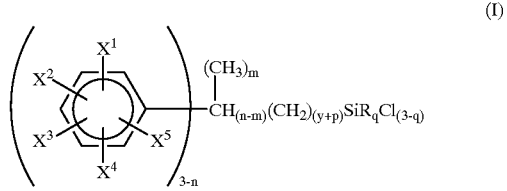

wherein m, p, and q are 0 or 1, respectively; n and y are 0 or 1, respectively; $X^1$, $X^2$, $X^3$, $X^4$, and $X^5$ which are same or different represent hydrogen, fluoro, chloro; R represents $C_1$–$C_{12}$ alkyl group; provided that if n is 0, m is 0 and if n is 1, at least two of $X^1$, $X^2$, $X^3$, $X^4$, and $X^5$ represent chloro or fluoro group.

2. Aryl substituted alkylsilanes according to claim 1 which is [(bis(2,5-dichlorophenyl)methyl] methyldichlorosilane.

3. Aryl substituted alkylsilanes according to claim 1 which is [(bis(fluorophenyl)methyl]methyldichlorosilane.

4. Aryl substituted alkylsilanes according to claim 1 which is (triphenylmethyl)dichlorosilane.

5. Aryl substituted alkylsilanes according to claim 1 which is (triphenylmethyl)trichlorosilane.

6. Aryl substituted alkylsilanes according to claim 1 which is [2,2-bis(2,5-dichlorophenyl)ethyl]trichlorosilane.

7. Aryl substituted alkylsilanes according to claim 1 which is (3,3-diphehylpropyl)trichlorosilane.

8. Aryl substituted alkylsilanes according to claim 1 which is [3,3-(bis(fluorophenyl)propyl]trichlorosilane.

9. Aryl substituted alkylsilanes according to claim 1 which is (2,2-diphenylethyl)trichlorosilane.

10. Aryl substituted alkylsilanes according to claim 1 which is [2,2-bis(2,5-dichlorophenyl)ethyl]trichlorosilane.

11. Aryl substituted alkylsilanes according to claim 1 which is [2,2-bis(2,4-dichlorophenyl)ethyl]trichlorosilane.

12. Aryl substituted alkylsilanes according to claim 1 which is [2,2-bis(trichlorophenyl)ethyl]trichlorosilane.

13. Aryl substituted alkylsilanes according to claim 1 which is [2,2-bis(2,3,4,5-tetrachlorophenyl)ethyl]trichlorosilane.

14. Aryl substituted alkylsilanes according to claim 1 which is (3,3-diphenylpropyl)trichiorosilane.

15. Aryl substituted alkylsilanes according to claim 1 which is [3,3-bis(fluorohenyl)propyl]trichlorosilane.

16. Aryl substituted alkylsilanes according to claim 1 which is (3,3-ekphenylbutyl)trichlorosilane.

17. Aryl substituted alkylsilanes according to claim 1 which is [3,3-bis(2,4-dichlorophenyl)butyl]trichlorosilane.

18. A method to prepare aryl substituted alkylsilanes represented by formula I

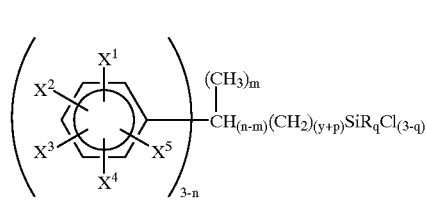

which comprises reacting substituted benzene of the formula II with aryl substituted alkylsilanes of the formula III

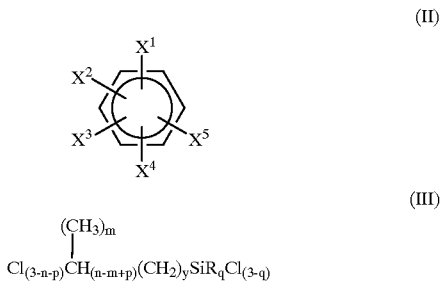

in the presence of Lewis acid catalyst at the reaction temperature between 0 and 200° C.

(whrein m, p, and q are 0 or 1, respectively; n and y are 0 or 1, respectively; $X^1$, $X^2$, $X^3$, $X^4$, and $X^5$ which are same or different represent hydrogen, fluoro, chloro; R represents $C_1$–$C_{12}$ alkyl group; provided that if n is 0, m is 0 and if n is 1, at least two of $X^1$, $X^2$, $X^3$, $X^4$, and $X^5$ represent chloro or fluoro group).

19. The method according to claim 18, wherein the Lewis acid is aluminum chloride or aluminum.

20. The method according to claim 19, wherein the molar ratio of substituted benzene of formula II to aryl substituted alkylsilane of formula III is 1 to 20 and the Lewis acid is used in the amount of 1–100 mol % of (polychloroalkyl)silanes of formula III.

* * * * *